(12) United States Patent
Kitahara et al.

(10) Patent No.: US 7,432,306 B2
(45) Date of Patent: Oct. 7, 2008

(54) METHOD FOR PREPARING NOVEL TRANSCRIPTION FACTORS AND USE

(75) Inventors: Takeshi Kitahara, Tokyo (JP); Hidenori Watanabe, Nagareyama (JP); Kunio Ando, Kawasaki (JP)

(73) Assignee: NRL Pharma, Inc., Kawasaki-shi (JP)

( * ) Notice: Subject to any disclaimer, the term of this patent is extended or adjusted under 35 U.S.C. 154(b) by 0 days.

(21) Appl. No.: 11/219,811

(22) Filed: Sep. 7, 2005

(65) Prior Publication Data

US 2007/0054966 A1 Mar. 8, 2007

(51) Int. Cl.
*A61K 31/075* (2006.01)
*C07C 43/30* (2006.01)

(52) U.S. Cl. .................... 514/717; 568/592

(58) Field of Classification Search ............... 568/591; 549/483

See application file for complete search history.

(56) References Cited

FOREIGN PATENT DOCUMENTS

EP       1 616 856 A        1/2006

OTHER PUBLICATIONS

Machine translation of JP 2005225851 A, published Aug. 25, 2005.*
Database WPI, Section Ch, Week 200560, Derwent Publications Ltd., London, GB; AN 2005-586473, XP002340064 -& JP 2005 225851 A (Kitahara T) Aug. 25, 2005; p. 13, tables; p. 17, tables; p. 18, reaction scheme.
K. Mori et al., *Tetrahedron Letters*, vol. 40, No. 14, 1984, pp. 2711-2720.
K. Mori et al., *Tetrahedron Letters*, vol. 24, No. 14, 1983, pp. 1547-1548.

* cited by examiner

*Primary Examiner*—Rosalynd Keys
(74) *Attorney, Agent, or Firm*—Birch, Stewart, Kolasch & Birch, LLP

(57) ABSTRACT

The present invention has an object to develop novel compounds which are effective for the therapy of syndrome X, cancer, myxedema, vascular chronic inflammation and the like, and furthermore prevent/treat the restenosis caused in an artery expansion by a balloon or a stent and have the activity facilitating regenerative medicine by inhibiting rejection of own cells or tissues to be transplanted and the method for preparing the same. Novel acetal derivatives obtained by acylating the hydroxyl group at the 2-position of the orcylaldehyde which ascochlorin and its analogs have and thereafter bonding an alcohol to the aldehyde group in the presence of a basic catalyst are found to achieve the object.

16 Claims, No Drawings

METHOD FOR PREPARING NOVEL TRANSCRIPTION FACTORS AND USE

BACKGROUND OF THE INVENTION

The present invention relates to a method for preparing novel transcription factors which modify the procedure of transcription of gene information in a messenger RNA and their use.

The leading cause of death in developed countries other than Japan is ischemic heart disease. Further, in Japan cancer is the leading cause of death. In the United States of America, ischemia heart disease occupied 60 to 70% of the causes of death for a long time but as the result of the enlightenment movement on an extensive scale by the government and medical institutions, the death due to ischemia heart disease was reduced in an about 40% range. Even at present, however, ischemic heart disease is the first cause of death and occupies 70% of causes of death in the Scandinavian countries such as Sweden and Norway to run ahead of others. Further, in developing countries such as China, the top of the causes of death is ischemic heart disease, and regardless of industrialized countries and developing countries, the development of methods of the therapy and prophylaxis of ischemic heart disease as well as malignant tumor, type II diabetes, cerebrovascular diseases, obesity and the like is rightly an urgent need.

Ischemic heart disease of a representative life style-related disease frequently causes sudden death, and thus is the target of fear for people in highly industrialized countries. Three major risk factors which cause its onset are (1) a hereditary predisposition, (2) an environmental factor such as smoking, lipid metabolic disorder and diet and (3) aging. Of them, the hereditary disposition and the aging are very difficult to control. On the other hand, a large majority of highly industrialized countries continues making an effort to socially reduce environmental risk-factors. For example, smoking is regarded as a bad habit, and tobacco is banished from the environment, and suits against tobacco companies are frequently started.

As to the therapy/prophylaxis of ischemic heart disease, only the environmental factor is controllable. Then, for the purpose of removing risk-factors from the environment, a number of methods such as (1) diet therapy, (2) excercise therapy and (3) drugs are advocated. As to the diet, people in developed countries come to avoid intake of foods containing a large amount of cholesterol. Beef and eggs are victimized as the representatives of such foods and their consumption tends to be decreased over a long period of time. Excess intake of energy due to overeating induces obesity. It has been clarified that obesity alone cannot become a risk-factor but obesity combined with insulin resistance (type II diabetes), hyperlipidemia or hypertension becomes to be a risk-factor which is called as syndrome X (also known as silent death syndrome, deadly quartet or visceral obesity) (Reaven G. M, Diabetes 37:159-1607, 1988). In the United States of America, in order to avoid obesity, exercise therapy such as jogging and fitness which accelerate the consumption of energy is prevailing.

Of environmental risks which cause ischemic heart disease, the serum cholesterol concentration shows the highest correlation. The serum cholesterol concentration as a risk-factor is shown by several criteria. In other words, the criterion is whether or not the serum cholesterol or the cholesterol present in serum low density lipoprotein (LDL) is higher than the normal value or whether or not the serum high density lipoprotein (HDL) is lower than the normal value. It is known that in both cases, the onset risk of ischemic heart disease increases depending on the concentration. Accordingly, the drug therapy of reducing hypercholesterolemia with serum cholesterol lowering agents is also adopted as the standard therapy preventing ischemia heart disease. The serum cholesterol lowering agents have had their effect so that they had come to the most successful drug among therapeutic agents. Above all, an inhibitor of hydroxyl-methylglutaryl coenzyme A (HMG-CoA) reductase which reduces hydroxymethylglutaryl coenzyme A to mevalonyl coenzyme A is the most successful drug which is the top sales among the global drug market. The annual turnover of statin has reached 40 billion US Dollars or more.

On the other hand, the elucidation of the mechanism has advanced how angina pectoris and myocardial infarction are caused. Up to the 1980s, the medical professionals thought that cholesterol accumulated into the arterial intima formed atheroma plaques that constrict/block the intravascular cavity leading to ischemia of myocardium. However, since the 1970s, several clinical studies had been performed based on the hypothesis that it is a thrombus which constricts/blocks the coronary blood flow and prevention of the formation of the thrombus could prevent/treat ischemic heart disease. For example, such clinical trials used aspirin which is an anti-inflammatory agent and has an action of inhibiting platelet-aggregation. Since aspirin induces a peptic ulcer during its chronic administration, it is very difficult to set dossier. In a long-term double blind clinical trials, aspirin was effective in some cases and was invalid in another trial, and thus aspirin has failed to obtain constant beneficial effect. After all, it seems likely that aspirin requires much higher doses to prevent arterial inflammation which frequently causes peptic ulcer and the smaller dose is not effective.

In the 1990s, instead of the concept that atheroma causes coronary ischemia, the hypothesis is presented that intra arterial blood vessel(s) induced by angiogenesi in atheroma rupture by inflammation and resulting blood clot occludes the blood stream. In other words, the hypothesis that inflammation of intra-arterial blood vessel(s) formed to nourish atheroma plaque(s) is causative of coronary heart disease (Ross R.: New England J. Med. 340:115-126, 1999) has been generally accepted. Therefore, the two major risk factors for coronary heart disease are hypercholesterolemia and chronic inflammation in atheroma plaque(s). It has been clarified from the epidemiological study that when the serum total cholesterol/HDL cholesterol level and the serum CRP level, the marker of chronic inflammation are both abnormally, the ratio of risk for myocardia infarction and cerebrovascular accidents are eight times higher than those being normal.

There is a therapeutic agent for improving the above described four disorders. However, as is clear from the fact that the co-administration of celibastatin-gemfibrozil induced rhabdomyolysis to threat lives, combined use of drugs may cause a danger of bringing about complicated interactions with each other. Thus, the number of drugs to be administered is preferably reduced. However, there is no drug which can treat the above described four disorders with single therapy.

There have been a number of therapies for the treatment of type II diabetes which does not requires daily insulin injections. It is known that type II diabetic patients frequently associate obesity at the onset, and its onset and obesity show a high correlation. Further, at the early stage of its onset, the obese patients show hyperinsulinemia and the type II diabetes is caused by the insufficiency in insulin action but not by that in its amount. Because the peripheral tissues in type II diabetes become resistant to the action of insulin. The first choice in treatment is diet therapy. Exercising enhances the peripheral sensitivity of insulin and is used together with the diet therapy.

If the cause of the onset and aggravation of type II diabetes are due to the insulin resistance in the peripheral tissue, the potentiation of the insulin sensitivity improves type II diabetes. In fact, one of the inventors has proved that 4-O-carboxymethylasco-chlorin (AS-6) of one of ascochlorin derivatives improves in the carbohydrate metabolism in hereditary obese diabetic mouse C57BL ksj (db/db), and the improvement is caused by the reduction in the insulin resistance of white adipose tissue (Hosokawa, Ando and Tamura; Diabetes, 34:267-274, 1985). Furthermore, the individual blood sugar levels of an AS-6 administered group and an AS-6 non-administered group and normal siblings and the carbohyrate metabolic capacity in the white adipose tissue are inversely correlated with a high correlation coefficient (r=−0.899), that is, the insulin resistance of the db/db mouse is caused by the disorder of energy metabolism of white adipose tissue and the improvement of energy metabolism of white adipose tissue by AS-6 reduces its insulin resistance. At present, it is clarified that when triglyceride is highly accumulated in the white adipose tissue, insulin resistance factors such as tumor necrosis factor-α and interleukin-1β which white adipocytes produce (Hotamisligil G. S., Sargaill N. S., Spiegelman B. M. et al: Science 259, 87-91, 1993) trigger the onset of type II diabetes. That is, it has been clarified that the white adipose tissue as well as the pancreatic Langerhans islet β cell is the target for the therapy of type II diabetes. Early in the mid-1980, however, the white adipose tissue was thought a mere store for triglyceridet and it was not anticipated that white adipose tissue plays a central role for a carbohydrate metabolism.

On the other hand, when attention is paid to cancer, it is clear that "surgical operation", "anticancer agent" and "radiotherapy" called as the three major therapies are not always satisfactory under the present situation. Above all, anticancer agents which lead to complete cure are rare in spite of the long history of anticancer chemotherapy. The representative cancers which anticancer agents can lead to complete cure are acute myelocytic leukemia, malignant lymphoma, childhood viral tumor and the like. The beneficial effect of anticancer agents cannot be expected for prostatic cancer, breast cancer, large bowel cancer, gastric cancer, hepatoma, pancreas cancer, brain tumor and the like which account for a large majority of cancers. Furthermore, most anticancer agents are highly cytotoxic and the cells which propagate vividly are more sensitive to anticancer chemotherapy nonspecifically. Thus, anticancer agents have a side effect of inhibiting the multiplication of epithelial cells of the small intestine and reducing leukocytes to lower immune potency.

A greater problem for anticancer chemotherapy is that cancer cells readily acquire resistance to anticancer agents. The anticancer chemotherapies used in combination. However, cancer acquires resistance to any combination of anticancer agents in a short period of time and the anticancer effect is normally lost. Although the mechanism for the acquisition of resistance to anticancer agents is being studied, no means to clinically avoid the resistance has been found.

It is known that the ascochlorin and its derivatives have a time-dependent efficacy. The condition of exhibiting the drug efficacy is that the blood concentration continues over the threshold but not toxic concentrations for a definite period of time. For example, when AS-6 is orally administered to an animal, its blood concentration rapidly rises over the effective concentration approaching up to the toxic concentrations. Along with this defect, AS-6 is quickly excreted, the short duration of threshold concentration and the oxidation of aldehyde group to a carboxylic acid are weak points of this derivative. The carboxylic acid of AS-6 is less effective in efficacy as compared to AS-6. Further, there is a defect such that since the blood concentration of AS-6 quickly rises up to a concentration of exhibiting toxicity, the toxicity to the liver is easily exhibited.

4-O-Methylascochlorin (MAC) of another ascochlorin derivative developed prior to AS-6 has a solubility in water less than 0.7 μg/ml and is extremely sparingly soluble in water, and additionally very poor bioavailability due to the low water solubility has been a disadvantage in exhibiting the drug efficacy. Thus, the orally administered MAC mostly passes right through the gastrointestinal tract and is excreted in feces. Since the duration of the effective blood concentration is short and the peak of the blood concentration is low in animals, the defect of MAC is that the efficacy, for example, the lowering rates of the serum total cholesterol, blood sugar are low.

In other words, in order for ascochlorin and its derivatives to exhibit their efficacy, the prerequisites are less toxicity and higher drug-efficacy than hitherto ascochlorin derivatives; that is the derivatives continue the blood concentrations over threshold and below toxic levels for a definite period of time.

It is the most important to investigate and develop therapeutic agents for improving the syndrome X is the search for single compound efficacious for hypercholesterolemia, hypertension, hyperglycemia. Furthermore, it is also one of the problems to develop anticancer agents which do not reduce immune potency and do not allow cancer cells to acquire resistance. 4-O-Methylascocholrin and 4-O-carboxymethylascochorin for which the present inventors obtained a patent are the derivatives by modifying the phenolic hydroxyl group at the 4-position of the orcylaldehyde in ascochlorin. More than twenty years have passed since acquisition of the patents for these derivatives. Further, a number of the derivatives obtained by modifying the hydroxyl group at the 4-position of the orcylaldehyde in ascochlorin with an alky group or an allyl group have been synthesized, and thus it would be difficult to synthesize novel derivatives merely by substituting the hydroxyl group at the 4-position of the aromatic ring which could be patented.

The ascochlorin series compounds have a property of exhibiting time-dependent efficacy. That is, the blood concentration of an active substance has to be lower than the concentration of exhibiting toxicity and, at the same time, has to continue for a definite period of time above the threshold of exhibiting the drug efficacy. On the other hand, 4-O-alkylascochlorins obtained by alkylating the hydroxyl group at the 4-position of ascochlorin which have been studied heretofore are hardly soluble in water due to their high fat-solubility. Additionally, the rate of dissolution of the molecule in water from the crystal lattice is extremely slow, and when the 4-O-alkylascochlorins are orally administered to a small animal such as a rat and a mouse at fasting stage, they mostly pass right through the gastrointestinal tract and are excreted in feces. In addition to the low bioavailability, their absorption from the gastrointestinal tract also varies depending on the presence or absence of food intake (Agr. Bio. Chem., 46: 775-781, 1982) because bile secreted by food intake stimulates the rate of their solubility in water. Poor reproducibility in animal experiments has been an obstacle to practical applications of the 4-Oalkylascochlorins.

The rate of dissolution of the molecule in water from the crystal lattice can be expedited by introducing a polar group in the molecule. In fact, 4-O-carboxymethylascocholorin obtained by substituting the hydrogen at the 4-position of ascochlorin is soluble in water at a concentration of 6% or more at a pH of 7.2 to 7.7 in the small intestine, and thus is quickly absorbed on oral administration. As a result, there has been a defect of exceeding the blood concentration of exhibiting toxicity in a human and an animal.

SUMMARY OF THE INVENTION

In order to develop therapeutic drugs for common diseases, the syndrome X and cancer by using ascochlorin and its analogs as the mother compounds, the following conditions have to be met. That is, novel derivatives should have the conditions that (1) they are synthesized at a low cost; (2) they are slowly and surely absorbed from the gastrointestinal tract; (3) they exhibit a serum cholesterol lowering action in animal experiments and a surely improving action to hereditary obese diabetic animal models, hypertensive animal models and the like; (4) they are effective in tumor bearing animal models; (5) they are transcription factors; (6) they have an anti-inflammatory action capable of treating/preventing vascular chronic inflammation and the like.

With these objects in view the present inventors have focused on the acetal derivative of the aldehyde group on the aromatic ring in ascochlorin series compounds and their derivatives and have tried to synthesize them. Surprisingly, the acetals have never been formed in the normal alcohol exchange reaction by an acid catalyst. However, it has been found that only when the phenolic hydroxyl group adjacent to the aldehyde group on the aromatic ring has been acylated, the acetalization of the aldehyde group occurs in the presence of a basic catalyst under novel conditions. With respect to ascochlorin and its analogs, acetal derivatives have not been reported, and the synthesized acetal derivatives are all novel compounds.

The novel acetal compounds of ascochlorin derivatives have physico-chemical properties as bulk drugs between MAC and AS-6. Accordingly, on oral administration, the acetal compounds are not so poorly absorbed as MAC but they are not so quickly absorbed as AS-6. Further, as the result of animal experiments and molecular biological study, the novel acetal compounds are inactive prodrugs. However, it has been clarified that they regenerate the aldehyde group in a living body to form a Schiff base with a serum protein, and when the Schiff base reaches a target organ or a target tissue, it becomes incorporated into a cell, and when incorporated into the cell, the serum albumin is digested and the ascochlorin or its derivatives having an aldehyde group is regenerated to exhibit the drug efficacy as a transcription factor. The drug efficacy is referred to exhibit a serum cholesterol lowering action, a metabolism improving action in a hereditary obese diabetic animal model, an antihypertensive action in a hypertensive animal model and an action of inhibiting fat accumulation in a healthy animal. Furthermore, it has been clear that the compounds of the present invention exhibit a prophylactic/therapeutic effect on arterial chronic inflammation, an improving effect on the onset of myxedema due to an insufficient thyroid hormone action, an anticancer action, a prophylaxis/therapy for the restenosis of an arterial cavity expanded by a balloon catheter or a stent and the reception of own grafted cells from stem cells externally differentiated and induced in regenerative medicine and the like, and thus the present invention has been completed.

The novel transcription factors of the present invention possess pharmacological properties indispensable to the therapy of life style-related diseases such as ischemic heart disease, type II diabetes, hypertension (cerebrovascular accidents), obesity and cancer.

The novel transcription factors of the present invention are expected to show a therapeutic effect on hypercholesterolemia, hyperglycemia, hypertension and obesity.

DETAILED DESCRIPTION OF THE INVENTION

The compounds of the present invention can be administered in any administration route accepted for the drugs provided in similar applications in the form of a pure product or a formulation of an appropriate pharmaceutical composition. Thus, their administration can be, for example, orally, nasally, parenterally or topically performed in the form of administration of a solid, a semisolid, a freeze-dried powder or a liquid such as a tablet, a pill, a capsule, a powder, a liquid and a solution, a suspension, an emulsion, a cream, a lotion, an aerosol, an ointment and a gel, preferably at an appropriate unit dose for administering an accurate volume at one time. This composition is composed of a single substance for normal pharmaceutical preparations or a filler and the compounds of the present invention, and may further contain other pharmaceuticals, a carrier, an absorption auxiliary and the like. A pharmaceutically acceptable composition generally comprises about 1 to 99% (by weight) of the compounds of the present invention and about 99 to 1% of appropriate drug additives depending on the type of the agent administered. This composition comprises about 5 to 75% of the compounds of the present invention as medical drugs and the rest of appropriate drug fillers. The effective dose per day of the compounds of the present invention for improving the state of a disease is 0.01 to 100 mg, preferably 0.1 to 10 mg per body weight-kg of an adult.

A preferred form of administration for diseases as explained in detail above is formulated in a manner such that the dose adjustably set according to the extent of the diseases can be selected. The most important thing in manufacturing pharmaceutical preparations is the restriction derived from the fact that the compounds of the present invention are fat-soluble. The ligand of the nuclear receptor super family is a fat-soluble hormone or a vitamin, and accordingly the compounds of the present invention are naturally fat-soluble. The additives pharmaceutically acceptable for oral administration are prepared by adding normally usable any filler such as mannitol, milk sugar, starch, magnesium stearate, saccharin sodium, talc, cellulose, glucose, gelatin, sucrose and magnesium carbonate. Such a composition takes the form of a liquid and a solution, a tablet, a pill, a capsule, a powder, a sustained release pharmaceutical preparation and the like.

The composition is preferably in the form of a tablet or a pill, and this composition comprises the compounds of the present invention and a filler such as milk sugar, sucrose and monobasic calcium phosphate, a disintegrator such as starch and its derivative, a lubricant such as magnesium stearate, a binder such as starch, acacia, polyvinylpyrrolidone, gelatin, cellulose and a derivative thereof, and furthermore a surface active agent having an action of wetting the particle surface of the compound of the present invention which is highly fat-soluble and water-repellent with water, a fat-soluble additive, bile acid, phospholipid and the like. It is particularly preferred that the composition comprises an aliphatic synthetic surface active agent or an organic solvent-soluble polymer auxiliary. Examples of these substances include, for example, acacia, sodium alginate, methylcellulose, carboxymethylcellulose, hydroxypropyl cellulose, polyvinylpyrrolidone, bentonite, sodium lauryl sulfate, polysorbate 80, a sorbitan fatty acid monoester and polyoxy 40 stearate.

The examples of the present invention will now be given below but it goes without saying that the present invention is not restricted by these examples.

EXAMPLE 1

Method for Synthesizing Diacyl Derivatives of Ascochlorin, Cilindochlorin, Ascofuranone, Chloronectin, LLZ-1272-a and LLZ-1272-d Ascochlorin and its analogs of 4-O-alkylascochlorins, 4-O-carboxyalkylascochlorins, ascofuranone, cylindrochlorin, chloronectin, LLZ-1272-a and LLZ-1272-d and the like were added to a pyridine/acetic anhydride mixture solution and left to stand at room temperature overnight. The amount of the acetic anhydride added in the pyridine/acetic anhydride mixture solution for acylating ascochlorin and its analogs was in slight excess per one hydroxyl group of the former on a molar basis. After left to stand overnight, the reaction solution was poured into water and about three parts in volume, based on one part in volume of the mixture solution, of ethyl acetate were added to the mixture solution, and the resulting mixture solution was vigorously agitated in a separatory funnel, and the upper layer of the ethyl acetate phase was dispensed. The lower layer was again extracted with ethyl acetate, and the ethyl acetate phases were combined. These combined ethyl acetate phases were washed with 1 N diluted hydrochloric acid and a saturated sodium hydrogen carbonate solution in the order named, and anhydrous sodium sulfate was added to the washed solution to dry it. The anhydrous sodium sulfate was removed by filtration and the filtrate was concentrated under reduced pressure to dryness to obtain a crude acylated product. The acylated product obtained by the present operation was nearly quantitative in yield and had very high purity, and thus could be used in the successive step without further purification.

EXAMPLE 2

Another Method for Preparing 2,4-Di-O-acetylascochlorin

Another method using acetyl chloride instead of acetic anhydride is as follows. Ascochlorin (0.300 g, 0.741 mmol) was dissolved in anhydrous pyridine (1.3 ml), and acetyl chloride (0.158 ml, 2.22 mmol) was added dropwise thereto while cooling in a water bath. The reaction solution was agitated at room temperature for four hours, and then a saturated $NaHCO_3$ aqueous solution (2 ml) was added thereto, and the resulting mixture solution was further agitated for 20 minutes. The reaction solution was diluted with water, and then extracted with ether, and the ether layer was washed with a saturated $CuSO_4$ aqueous solution, water and a saturated sodium chloride aqueous solution in the order named, and then dried with anhydrous sodium sulfate. After filtering the desiccant, the filtrate was concentrated under reduced pressure to obtain 0.320 g (88%) of 2,4-di-O-acetylasco-chlorin (as a colorless gum).

NMR ($CDCl_3$), 500 MHz): 0.17 (3H, s), 0.81 (3H, d, J=6.7 Hz), 0.84 (3H, d, J=6.7 Hz), 1.63 (1H, qd, J=13.0, 5.5 Hz), 1.86 (3H, s), 1.90-1.97 (2H, m), 2.34 (3H, s), 2.35 (3H, s), 2.36-2.43 (3H, m), 3.35 (2H, d, J=7.0 Hz), 5.25 (1H, t, J=7.0 Hz), 5.41 (1H, d, J=16.0 Hz), 5.87 (1H, d, J=16.0 Hz), 10.27 (1H, s)

EXAMPLE 3

In the past study, in the investigation of the acylation of ascochlorin and its analogs, it had been found that crystalline 4-O-acyl derivatives could be obtained. Even if 2,4-di-O-acetyl derivatives have been formed in the reaction solution, the acyl group at the 2-position was easily hydrolyzed to return to a hydroxyl group in the purification process. Accordingly, the 2,4-di-O-acyl derivatives which could not be obtained in a crystalline form have hardly been used as starting materials for novel derivatives. In this Example, in order to confirm the formation of the 2,4-di-O-acetyl derivatives, 2,4-di-O-acetylascochlorin (0.1 mmol) was dissolved in a solvent/catalyst of a methanol/triethyl-amine mixture solution for allowing the aldehyde group to react with a primary amine to effect aminocarbonylation, and left to stand at room temperature overnight to try to obtain 4-O-methylascochlorin by partial decomposition of the acyl groups. Surprisingly, the formed product was not 4-O-acetyl derivative but 4-O-acetylascochlorin dimethyl-acetal in which two molecules of methanol were added to the aldehyde group was quantitatively (0.095 mmol) formed. In order to confirm the acetal formation, when 2,4-di-O-acetylascochlorin (0.1 mmol) was dissolved in a triethyl-amine/ethanol mixture solution and treated in the same manner as in the case of using the methanol/triethylamine mixture solution, it was confirmed that 4-O-acetylasco-chlorin diethylacetal was quantitatively (0.098 mmol) formed. Further, when 4-O-acetylascochlorin dimethyl-acetal was dissolved in a diluted hydrochloric acid/methanol solution and hydrolyzed, 4-O-acetylascochorin was formed. Thus, it was confirmed that the compounds which ascochlorin and its analogs having hydroxyl groups at the 2- and 4-positions of the aromatic ring react with excess acetic anhydride in a pyridine solvent to form are the 2,4-diacetyl derivatives, and the acetal derivatives are formed under mild conditions. Naturally, when the aldehyde group was protected with an acetal and allowed to react with a primary amine in the presence of a basic catalyst, no Schiff base was formed.

Preparation of Intermediates

| Name | Structural Formula | Yield | Purity | Note |
|---|---|---|---|---|
| 2,4-O-Di-acetyl-ascochlorin | (structure) | 97% | ◎ | Solid, TLC, NMR: Good purity, Used without purification |

| Name | Structural Formula | Yield | Purity | Note |
|---|---|---|---|---|
| 4-O-Acetyl-ascochlorin | (Acetic Anhydride Method) | 87% | ◎ | Crystalline, TLC, NMR: Good purity, Used without purification, Two preparation methods |
|  | (Acetyl Chloride Method) | —% | ◎ | Crystalline, Yield: not measured, TLC, NMR: Good purity, Used without purification |
| 2-O-Acetyl-4-O-methyl-ascochlorin |  | Almost Quantitative | ◎ | Oily, TLC, NMR: Good purity, Used without purification |
| 2,4-O-Di-acetylasco-furanone |  | Almost Quantitative | ◎ | Oily, TLC, NMR: Good purity, Used without purification |

EXAMPLE 4

On the other hand, the 4-O-monoacetyl derivatives does not form the acetals under the conditions for forming the acetals with the use of the 2,4-di-O-acetyl derivatives as the starting substances (that is, dissolving the 4-O-monoacetyl derivatives in a triamine/methanol mixture solvent and leaving the mixture to stand). However, when the 2-O-acetyl derivatives obtained by acetylating 4-O-methylascochlorin and 4-O-carboxymethylascochlorin with acetic anhydride in a pyridine solvent are dissolved in a triethylamine/alcohol solvent and the resulting mixture solution is left to stand at room temperature overnight, the acetals are formed. Thus, in order to form an acetal, it is necessary that the hydroxyl group adjacent to the aldehyde group has been acylated. When ascochlorin and its analogs whose hydroxyl group at the 2-postion had been acylated were condensed with an alcohol by using a basic catalyst in the presence or absence of a reaction solvent, the acetal derivatives were quantitatively formed as shown in Tables 1 to 3.

TABLE 1

Acetal Formation of Acetylascochlorins

| Name | Structural Formula | Yield | Purity | Note |
| --- | --- | --- | --- | --- |
| 4-O-Acetyl-ascochlorin dimethylacetal | | 81% | ◎ | Compound 1 |
| 4-O-Acetyl-ascochlorin diethylacetal | | Almost Quantitative | ◎ | Compound 2 |
| 4-O-Methyl-ascochlorin diethylacetal | | 71% | ◎ | Compound 3 Crystalline |
| 4-O-Acetyl-ascofuranone diethylacetal | | 50% | ◎ | Compound 4 |
| 4-O-Methyl-ascochlorin dibutylacetal | | 51% | ◎ | Compound 5 |
| 4-O-Methyl-ascochlorin propylene glycolacetal | | 61% | ◎ | Compound 6 |

TABLE 2

Infrared Absorption Spectral Data of Ascochlorins

| Acetal | Absorption Maximum (cm$^{-1}$) |
|---|---|
| 4-O-Acetylascochlorin dimethylacetal | 3290, 2972, 1778, 1711, 1415, 1371, 1231, 1200, 1108, 1055, 968 |
| 4-O-Acetylascochlorin diethylacetal | 3264, 2975, 1778, 1712, 1414, 1371, 1327, 1231, 1200, 1101, 1048, 1003 |
| 4-O-Methylascochlorin Diethylacetal | 3289, 2977, 2933, 1703, 1608, 1575, 1449, 1408, 1388, 1373, 1326, 1108, 1069, 1053, 979 |
| 4-O-Acetylascofuranone diethylacetal | 2978, 1752, 1638, 1373, 1196, 1050, 998, 752, 664 |
| 4-O-Methylascochlorin dibutylacetal | 3303, 2959, 2872, 1712, 1605, 1571, 1454, 1405, 1328, 1227, 1107, 970 |
| 4-O-Methylascochlorin propyleneglycolacetal | 3315, 2972, 2870, 1710, 1573, 1456, 1396, 1331, 1238, 1110, 987 |

TABLE 3

NMR Data of Ascochorin Acetals (Chemical Shift: ppm)

| Compound No. | 2-OH | —CH(OMe)$_2$ | —CH(OCH$_3$)$_2$ | —OCOCH$_3$ |
|---|---|---|---|---|
| 1 | 9.21 | 5.65 | 3.41 | 2.32 |

| Compound No. | 2-OH | —CH(OEt)$_2$ | —CH(OCH$_2$CH$_3$)$_2$ | —OCOCH$_3$ | —CH(OCH$_2$CH$_3$)$_2$ |
|---|---|---|---|---|---|
| 2 | 9.44 | 5.76 | 3.54 | 2.31 | 1.24 |
| 3 | 9.32 | 5.76 | 3.65 |  | 1.24 |
| 4 | 9.40 | 5.76 | 3.64 | 2.31 | 1.24 |

| Compound No. | 2-OH | —CH(OBu)$_2$ | —CH(OCH$_2$—Pr)$_2$ | —CH(OC$_3$H$_6$—CH$_3$)$_2$ |
|---|---|---|---|---|
| 5 | 9.31 | 5.74 | 3.57 | 0.89 |

| Compound No. | 2-OH | —CH(—OC$_3$H$_6$O)— | —CH(—OCH$_2$CH$_2$CH$_2$O)— |
|---|---|---|---|
| 6 | 8.82 | 5.81 | 4.30, 3.98 |

EXAMPLE 5

In general, acetal formation reaction uses an alcohol exchange reaction in the presence of an acid catalyst. Since direct acetal formation with an alcohol by a base catalyst which is a reaction not existed before is considered, the reaction mechanism in the case of the 4-O-carboxymethylascochlorin 2-O-acetyl derivative was presumed.

Mechanism of Acetal Formation

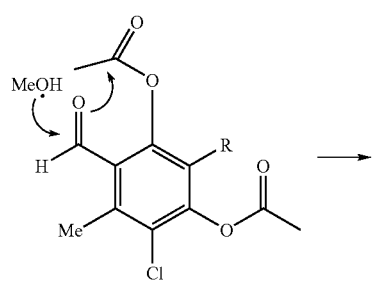

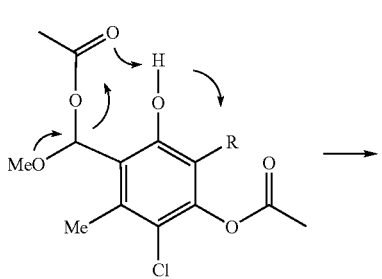

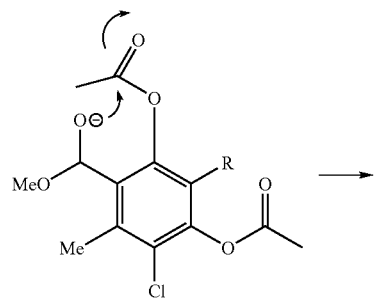

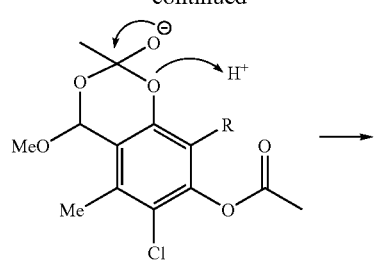

-continued

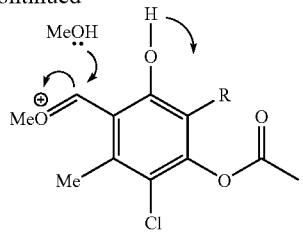

That is, it has been presumed that after addition of methanol to the aldeyde group, together with nucleophilic reaction to the adjacent acetyl group of a mixed acid anhydride and successive transition of the acetyl group and elimination of the acetoxy group, the second addition of methanol occurs to form an acetal.

EXAMPLE 6

Mouse Serum Cholesterol Lowering Action

Thirty 5-week-old ICR male mice were bred by allowing mouse standard feed and water ad libitum. The mice were randomly classified into three groups, and one group was taken as a control group to which no drug was administered, and feed containing 0.1% of 4-O-methylasco-chlorin diethylacetal (MAC-DEA) and feed containing 0.05% of MAC-DEA were given to the other two groups, respectively. The body weight, the intake of feed and the amount of drinking water were measured every other day. One week after giving feed, blood was collected and the total cholesterol in serum and the neutral fat were determined.

TABLE 4

Mouse Serum Cholesterol Lowering Action

| | Increase in Body Weight (g/mouse) | Total Cholesterol in Serum (mg/dl) | Rate of Change (%) |
|---|---|---|---|
| Control Group | 6.7 | 118 | |
| MAC-DEA 0.05% Group | 7.1 | 97 | −17.8 |
| MAC-DEA 0.1% Group | 6.9 | 90 | −23.7 |

Average value of 10 mice in each group

EXAMPLE 7

Eighteen 7-week-old male db/db mice were bred for one week by allowing mouse standard feed and water ad libitum. The mice were randomly classified into three groups of six mice and each group was housed in a urine collection rat cage and the intake of feed, the amount of drinking water, the amount of urine and the amount of urine sugar excreted were determined everyday. Feed CE-2 was given to the first group as a control group, and feed CE-2 mixed with 0.05% of 4-O-methylascochlorin diethylacetal (MAC-DEA) and feed CE-2 mixed with 0.1% of MAC-DEA were given to the second group and the third group, respectively. The mice were allowed feed and drinking water ad libitum and on the 7th day, blood was collected and the blood sugar, the serum neutral fat and the serum insulin were determined.

TABLE 5

Action of MAC-DEA on db/db Mouse

| | Control Group | MAC-DEA 0.05% Group | MAC-DEA 0.1% Group |
|---|---|---|---|
| Increase in Weight (g/mouse) | 5.1 | 5.0 | 4.8 |
| Intake of Feed (g/mouse) | 6.9 | 6.9 | 6.4 |
| Amount of Drinking Water (ml/mouse) | 7.7 | 5.4 | 3.2 |
| Amount of Urine (ml/mouse) | 4.1 | 2.5 | 1.7 |
| Amount of Urine Sugar Excreted (mg/dl) | 672 | 47 | 10 |
| Blood Sugar (mg/dl) | 416 | 273 | 239 |
| Serum Neutral Fat (mg/dl) | 517 | 259 | 248 |
| Serum Insulin (·U/ml) | 213 | 175 | 132 |

EXAMPLE 8

Under the Nembutal anesthesia the right kidneys of 24 Wister-Imamichi male rats each having an average weight of about 250 g were removed and the wound was sutured, and the rats were fed for two weeks by allowing diet and drinking water ad libitum. Eighteen rats in good health whose wound had completely healed were selected and used for the experiment. The rats were randomly allocated into three groups of six rats, and 10 mg/kg of the acetal (AC-PG) obtained by bonding propylene glycol to the aldehyde group of 4-O-acetylascochlorin was orally administered to the first group, 5 mg/kg of AC-PG was orally administered to the second group and a AC-PG suspended in 0.2% Tween aqueous solution as a vehicle. The vehicle alone was orally administered to the third group as a control group. On starting the experiment, the rats were allowed feed CE-2 and a 1% sodium chloride aqueous solution ad libitum and 5 mg/kg of deoxycorticosterone acetate was subcutaneously administered once a week. The consumption of the 1% sodium chloride aqueous solution and the amount of urine were determined everyday, and the blood pressure and the body weight were measured once a week. The Table shows the increase in body weight, the average amount of drinking water per day, the blood pressure and the total cholesterol in serum 42 days after starting the experiment.

TABLE 6

Influence of AC-PG on Hypertension Rat Model

| | Control Group | AC-PG 5 mg/kg | AC-PG 10 mg/kg |
|---|---|---|---|
| Increase in Body Weight (g/rat) | 45 | 62 | 98 |
| Amount of Drinking Water (ml/rat) | 86 | 41 | 25 |
| Blood Pressure (mmHg) | 189 | 142 | 131 |
| Serum Cholesterol (mg/dl) | 217 | 162 | 116 |

EXAMPLE 9

Under the Nembutal anesthesia the right kidneys of 40 Wister-Imamichi male rats each having an average body weight of about 250 g were removed and the rats were fed for two weeks by allowing feed and drinking water ad libitum.

Thirty-six rats in good health whose wound had completely healed were selected and used for the experiment. On starting the experiment, the rats were allowed diet CE-2 and a 1% sodium chloride aqeuous solution ad libitum and subcutaneously injected with 5 mg/kg of deoxycorticosterone acetate once a week. The rats were randomly allocated into three groups of six rats, and 10 mg/kg of the acetal (AC-PG) obtained by bonding propylene glycol to the aldehyde group of 4-O-acetylascochlorin was orally administered to the first group, 5 mg/kg of AC-PG was orally administered to the second group and the vehicle a 0.2% Tween-80 aqueous solution alone was orally administered to the third to sixth groups. On the 42nd day after starting of the experiment, the administration of deoxycorticosterone acetate to fourth to sixth groups was stopped and simultaneously the drinking water was changed from the 1% sodium chloride aqueous solution to tap water. Simultaneously, oral administration of 5 mg/kg of AG-PG to the fourth group and oral administration of 10 mg/kg of AG-PG to the fifth group were started and the experiment was completed after 56 days. To the third and sixth groups, a 0.2% Tween-80-containing aqueous solution was administered over the entire experimental period. The blood pressure and the body weight were determined once a week. On the 56th day, the mesenteric arteries were removed and subjected to fat dyeing and the aneurysms dyed in orange were counted. The Table shows the number of aneurysms per mesenteric artery.

TABLE 7

Blood Pressure and Number of Aneurysms per Mesenteric Artery of Prophylactic Group and Therapeutic Group

| | | Blood Pressure (mmHg) | Number of Aneurysms |
|---|---|---|---|
| Therapeutic Group | AC-PG 5 mg/Kg | 133 | 15 (−55%) |
| | AC-PG 10 mg/Kg | 138 | 2 (−94%) |
| | Control | 159 | 33 |
| Prophylactic Group | AC-PG 5 mg/Kg | 165 | 32 (−60%) |
| | AC-PG 10 mg/Kg | 134 | 27 (−65%) |
| | Control | 195 | 78 |

EXAMPLE 10

Under the diethyl ether anesthesia the carotid arteries of 18 Wister-Imamichi male rats each having an average body weight of about 250 g were exfoliated to prepare artery exfoliated rats which were models of restenosis (Fraser-Smith E B: J. Pharmcol. Exp. Ther., 275(3): 1204-8, 1995 December:). The rats were randomly classified into three groups of six rats and for two weeks, 50 mg/kg of the acetal (AS-6-DM) obtained by bonding methanol to the aldehyde group of 4-O-carboxymethylasco-chlorin was orally administered to the first group, 25 mg/kg of AS-6-DM were orally administered to the second group and a 0.2% Tween-80 aqueous solution alone was orally administered to the third group as a control. After two weeks, the carotid arteries were removed, fixed with formalin and subjected to HE staining and the thickness of the part most advanced in arterial fat-thickening was measured under a microscope and the inhibition of fat-thickening was compared by taking the thickness in the control group (the thickness of the fat-thickened carotid artery in the exfoliated portion minus the thickness of the artery in normal health) as 100%.

TABLE 8

Influence of AS-6-DM on Arterial Fat-Thickening

| | Inhibition Ratio (%) |
|---|---|
| AS-6-DM 50 mg/kg | 81 |
| AS-6-DM 25 mg/kg | 56 |

EXAMPLE 11

Thirty 5-week-old ICR male mice were randomly classified into six groups and all mice were fed for one week by allowing mouse standard diet CE-2 (a product of Japan CLEA Co., Ltd.). Then, the mice in the first to third groups were intravenously injected with 50 mg/kg of streptozotocin and after one week, blood was collected from the orbit and the blood sugar and the serum insulin were determined to confirm the onset of insulin-dependent diabetes. Ten days after the streptozotocin injection, pancreatic Langerhans islets were removed from the age-matched normal mice in the fourth to sixth groups and 20 pancreatic Langerhans islets were subcutaneously transplanted in the back of each of the diabetic mice. Immediately after transplantation, diet CE-2 containing 0.1% of MAC-DE was given to the first group, diet CE-2 containing 0.05% of MAC-DE was given to the second group and CE-2 was given to the third group. The diabetic mice were further fed for 60 days, and blood was collected from the orbit and the blood sugar and the serum insulin were determined every 15 days.

TABLE 9

Blood Sugar and Insulin of Syngeneic Langerhans Islet Transplanted Mouse

| | | Day 0 | Day 15 | Day 30 | Day 45 | Day 60 |
|---|---|---|---|---|---|---|
| Control Group | Blood Sugar | 534 | 270 | 390 | 564 | 551 |
| | Insulin | <2 | 2 | 2 | <2 | <2 |
| MAC-DE 0.05% | Blood Sugar | 566 | 143 | 148 | 125 | 118 |
| | Insulin | <2 | 5 | 5 | 6 | 6 |
| MAC-DE 0.1% | Blood Sugar | 583 | 121 | 118 | 119 | 131 |
| | Insulin | <2 | 5 | 6 | 6 | 6 |

Blood Sugar: mg/dl,
Insulin: ·U/ml

EXAMPLE 12

Thirty 5-week-old ICR male mice were randomly classified into three group of ten mice, and mouse standard diet CE-2 (a product of Japan CLEA Co., Ltd.) was given to the first group, and diet CE-2 containing 0.1% of 4-O-methylascochlorin diethylacetal (MAC-DE) was given to the second group and diet CE-2 containing 0.05% of MAC-DE was given to the third group and the mice were continued to be fed. The final body weight and the increase in body weight showed an inhibitory trend in the two MAC-DE groups compared to the control group but statistically there was no significant difference. After 13 weeks, the liver and the epididymal adipose tissue were removed from the mice and lipid was extracted by the Folch method and the triglyceride content was determined. As a result, the triglyceride content in the 0.05% MAC-DE group was reduced 27%, and the triglyceride content in the 0.1% MAC-DE group was reduced 35%. From this fact it would be understood that MAC-DE inhibits fat accumulation.

EXAMPLE 13

Enhancement of Thyroid Hormone Activity in Trans-activation Assay

The compounds of the present invention do not exhibit the thyroid hormone activity in the transactivation gene reporter assay for thyroid hormone. However, their mixing with a small amount of thyroid hormone enhanced the expression of a reporter gene. That is, when the reporter gene plasmid whose expression is controlled by a thyroid hormone response element and the thyroid hormone expression plasmid were introduced in COS-1 cells and thereafter the introduced cells were treated with thyroid hormone and the compounds of the present invention, the amount of expression of the reporter gene increased. This result shows that the compounds of the present invention are not agonists for the thyroid hormone nuclear receptor and enhance the gene expression through a cofactor in the process of transcription of the thyroid hormone activity.

EXAMPLE 14

Thirty 5-week-old ddY male mice were randomly classified into three groups of ten mice and fed for 13 weeks by allowing feed and water ad libidum. Meanwhile, the mouse standard diet CE-2 (a product of Japan CLEA Co., Ltd.) was given to the first group, and diet CE-2 containing 0.1% of 4-O-methylascochlorin diethylacetal (MAC-DE) was given to the second group of mice and diet CE-2 containing 0.05% of MAC-DE was given to the third group. The final body weight and the increase in body weight showed an inhibitory trend in two MAC-DE groups compared to the control group but statistically there was no significant difference. After 13 weeks, the livers and the epididymal adipose tissues were removed from the mice and lipid was extracted by the Folch method and the triglyceride content was determined. As a result, the triglyceride content in the 0.05% MAC-DE group was reduced 27%, and the neutral fat content in the 0.1% MAC-DE group was reduced 35%. From this fact it would be understood that MAC-DE inhibits internal fat accumulation.

EXAMPLE 15

Eighteen five-week-old ICR male mice were subcutaneously inoculated with $10^6$ cells of Ehrlich ascites carcinoma intraperitoneally and after 24 hours, and the mice were classified into three groups of six mice, and 4-O-methylascochlorin diethylacetal (MAC-DE) was suspended in 0.2% Tween-80 and 1 mg/kg and 4 mg/kg were orally administered to the first group and the second group twice a day at 9:00 and 20:00, respectively, and a MAC-DE-free Tween-80 aqueous solution was given to the third group as a control group. The administration was continued for successive 7 days and after completion of the administration, the mice were fed for two weeks. On the 21st day, a nodular tumor was removed from the mice and the body weight was determined and the effect of MAC-DE on the inhibition of tumor growth was examined.

As would be clear from Table 10, MAC-DE significantly inhibits the growth of Ehrlich carcinoma.

TABLE 10

Effect of MAC-DE on Inhibition of Ehrlich Solid Tumor

|  | Increase in Body Weight (g/mouse) | Weight of Tumor (g/mouse) | Inhibition Ratio (%) |
| --- | --- | --- | --- |
| MAC-DE 1 mg/kg | 10.8 | 0.25 | 81 |
| MAC-DE 4 mg/kg | 9.2 | 0.06 | 96 |
| Control Group | 9.6 | 1.34 | — |

The present invention provides novel therapeutic agents for atherosclerosis, hypercholesterolemia, hypertension, insulin-independent diabetes (also called as type II diabetes), chronic inflammation, myxedema, malignant tumor and the like and is additionally useful for the syndrome of multiple risk factors (syndrome X) for which no appropriate therapeutic means has existed, the prevention of the restenosis of an arterial cavity expansion by a stent and a balloon catheter and the security of take of a graft in regenerative medicine.

What is claimed is:

1. A method for synthesizing a novel acetal compound which comprises acylating two phenolic hydroxyl groups of a wholly substituted aromatic aldehyde of a metabolite of filamentous fungi having a sesquiterpene side chain at the 3-position, ascochlorin, cylindrochlorin, ascofuranone, chloronectin, LLZ-1272-α, LLZ-1272-δ or the like, and then reacting the resulting product with an alcohol in the presence of a base to give said acetal compound.

2. A method for synthesizing a novel acetal compound which comprises substituting the hydrogen of the phenolic hydroxyl group at the 4-position of ascochlorin, cylindrochlorin, ascofuranone, chloronectin, LLZ-1272-α, LLZ-1272-δ or the like with an alkyl group and acylating the phenolic hydroxyl group at the 2position to give an aromatic aldehyde derivative, and reacting said derivative with an alcohol in the presence of a base to give said acetal compound.

3. A novel acetal compound obtainable by the method according to claim 1.

4. A novel acetal compound obtainable by the method according to claim 2.

5. A pharmaceutical composition which comprises an effective amount of a novel acetal compound according to claim 3 and a pharmaceutically acceptable carrier.

6. A pharmaceutical composition which comprises an effective amount of a novel acetal compound according to claim 4 and a pharmaceutically acceptable carrier.

7. A method of using a pharmaceutical composition as a therapeutic/prophylactic drug for diabetes comprising:
   administering a composition according to claim 5 or 6 to a patient in need thereof.

8. A method of using a pharmaceutical composition as a therapeutic drug for atherosclerosis comprising:
   administering a composition according to claim 5 or 6 to a patient in need thereof.

9. A method of using a pharmaceutical composition as a serum cholesterol lowering agent comprising:
   administering a composition according to claim 5 or 6 to a patient in need thereof.

10. A method of using a pharmaceutical composition as a novel therapeutic drug for syndrome X comprising:
    administering a composition according to claim 5 or 6 to a patient in need thereof.

11. A method of using a pharmaceutical composition as a novel therapeutic drug for hypertension comprising:
   administering a composition according to claim 5 or 6 to a patient in need thereof.

12. A method of using a pharmaceutical composition as a novel therapeutic drug for myxedema comprising:
   administering a composition according to claim 5 or 6 to a patient in need thereof.

13. A method of using a pharmaceutical composition as a novel anti-inflammatory agent for treating chronic inflammation comprising:
   administering a composition according to claim 5 or 6 to a patient in need thereof.

14. A method of using a pharmaceutical composition as a novel anticancer agent comprising:
   administering a composition according to claim 5 or 6 to a patient in need thereof.

15. A method of using a pharmaceutical composition as a therapeutic/prophylactic drug for the restenosis of an arterial cavity expanded by a balloon catheter or a stent comprising:
   administering a composition according to claim 5 or 6 to a patient in need thereof.

16. A method of using a pharmaceutical composition as a take promoter which is administered to a recipient in order to allow cells or tissues which are differentiated and induced from a stem cell and which are transplanted in said recipient to take in performing regenerative medicine comprising:
   administering a composition according to claim 5 or 6 to a patient in need thereof.

* * * * *